United States Patent [19]

Joseph et al.

[11] Patent Number: 5,489,371
[45] Date of Patent: Feb. 6, 1996

[54] SENSOR FOR ELECTROCHEMICAL MEASUREMENTS

[75] Inventors: Jose P. Joseph, Palo Alto; Arvind Jina, Redwood City; Michael J. Tierney, San Jose, all of Calif.

[73] Assignee: Teknekron Sensor Development Corporation, Menlo Park, Calif.

[21] Appl. No.: 37,016

[22] Filed: Mar. 25, 1993

Related U.S. Application Data

[63] Continuation-in-part of Ser. No. 743,436, Aug. 8, 1991, abandoned.

[51] Int. Cl.$^6$ .................................. G01N 27/403
[52] U.S. Cl. .................. 204/415; 204/400; 204/412; 324/698
[58] Field of Search ................. 204/409, 411, 204/412, 415, 400; 324/698

[56] References Cited

U.S. PATENT DOCUMENTS

| | | | |
|---|---|---|---|
| 2,752,566 | 6/1956 | Quinton | 324/698 |
| 2,913,386 | 11/1959 | Clark, Jr. | 204/195 |
| 3,181,058 | 4/1965 | Gulbrandsen | 324/698 |
| 3,260,656 | 7/1966 | Ross, Jr. | 204/1 |
| 3,264,557 | 8/1966 | Heeps | 324/698 X |
| 3,711,395 | 1/1973 | Plank et al. | 204/195 P |
| 4,313,086 | 1/1982 | Baum | 324/698 X |
| 4,638,305 | 1/1987 | Sutton | 340/620 |
| 4,729,824 | 3/1988 | Giner | 204/415 |
| 4,741,204 | 5/1988 | Luck et al. | 436/61 |
| 4,744,870 | 5/1988 | Kauffman | 204/153.2 |
| 4,961,163 | 10/1990 | Bryan et al. | 364/550 |
| 5,032,363 | 7/1991 | Simon et al. | 422/82.03 |

*Primary Examiner*—John Niebling
*Assistant Examiner*—William T. Leader
*Attorney, Agent, or Firm*—Limbach & Limbach; Ronald L. Yin

[57] ABSTRACT

This invention relates to a sensor for the direct and continuous measurement of the electrochemical properties of compounds in a high resistivity liquid. The sensor has a housing which includes a porous hydrophilic membrane which may be made of a ceramic, and contains an electrolytic solution. The membrane permits the passage of a portion of the electrolytic solution into the pores thereby facilitating the formation of an interface between the electrolytic solution and the high resistivity liquid and allowing extraction of the compounds in the high resistivity liquid into the electrolytic solution. A porous sensing electrode is positioned directly on the membrane for detecting and measuring the concentration of the compounds extracted from the high resistivity fluid.

12 Claims, 3 Drawing Sheets

5,489,371

SENSOR FOR ELECTROCHEMICAL MEASUREMENTS

This is a continuation-in-part application of a application Ser. No. 07/743,436, filed on Aug. 8, 1991.

TECHNICAL FIELD

This invention relates to a sensor which is useful for direct measurement, without any sample preparation of electrochemical properties for non-conducting or low conducting fluids. For example, determination of oil quality properties can be made.

BACKGROUND OF THE INVENTION

Electrochemical cells to detect and determine the concentration of electrochemically active species (the analyte) in solution by measuring a voltage, a current or the conductance of the solution (hereinafter: "Electrical Properties") between two electrodes are well known in the art. In these solutions, electrochemical measurement is facilitated by charged ions moving relatively freely (i.e. encountering low resistance) in the solution.

Measurements of Electrical Properties is used to monitor many electroactive materials. However, prior art electrochemical cell has been used on-line for only a solution having high conductivity. The prior art electrochemical cell is placed in the solution having high conductivity. With the solution having high conductivity or low resistance, the electrical current or the voltage between electrodes (in a potentiometric measurement) can be measured with relatively low generation of electrical noise interference. Changes in the voltage or current, resulting from changes of the concentration of the analyte at the electrode-solution interface, can be detected. Changes in the conductivity, resulting from changes in the concentration of the analyte in the bulk of the solution, can also be detected. Thus, the signal to noise ratio is high.

For non-conducting or low conducting solutions (hereinafter: "high resistivity liquid"), such as oils, electrochemical cells were ineffective for on-line detection and measurement of analytes dissolved in these solutions. With the solution having high impedance, the amount of electrical noise obscures any reading of changes in the signal (current or voltage).

In order to detect and measure the concentration of analytes in high resistivity liquids, such as oil, a measured amount of the solution is placed in a polar solvent which has increased electrical conductivity to enable effective electrochemical measurements. An electrochemical measurement is made as described above. Thereafter, another measured amount of the solution is placed in the same polar solvent, and a second measurement made. The change in the electrochemical measurement is an indication of change in the concentration of the analyte. See U.S. Pat. Nos. 2,752,566; 3,264,557; 4,313,086; 4,638,305; 4,741,204; and 4,744,870. In U.S. Pat. No. 3,181,058 reference is made to the direct measurement of a test substance wherein an amount of polar solvent is poured into the test substance in order to increase its conductivity. However, there is no disclosure of continuous direct measurement (without sample pre-treatment) of the concentration of analytes in high resistivity liquids.

As can be seen from the foregoing, such a prior art method does not permit the on-line measurement of the concentration(s) of analyte(s) in high resistivity solutions.

SUMMARY OF THE INVENTION

The present invention is directed to a sensor for direct electrochemical measurement in a high resistivity liquid. This sensor has a housing including a porous membrane for containment of an electrolytic solution. The housing with the membrane is immersed in the high resistivity fluid. The membrane is a hydrophilic membrane permitting the passage of a portion of the electrolytic solution into the pores. A plurality of electrodes is adapted for immersion in the electrolytic solution for measuring the electrochemical properties of substances extracted into the electrolytic solution from the high resistivity liquid. The sensor design obviates the use of a tedious pre-extraction of the test sample and is therefore highly suited for direct in situ monitoring of the presence and concentration of substances in high resistivity liquids, such as oil.

DESCRIPTION OF THE PREFERRED EMBODIMENT

Figure 1:
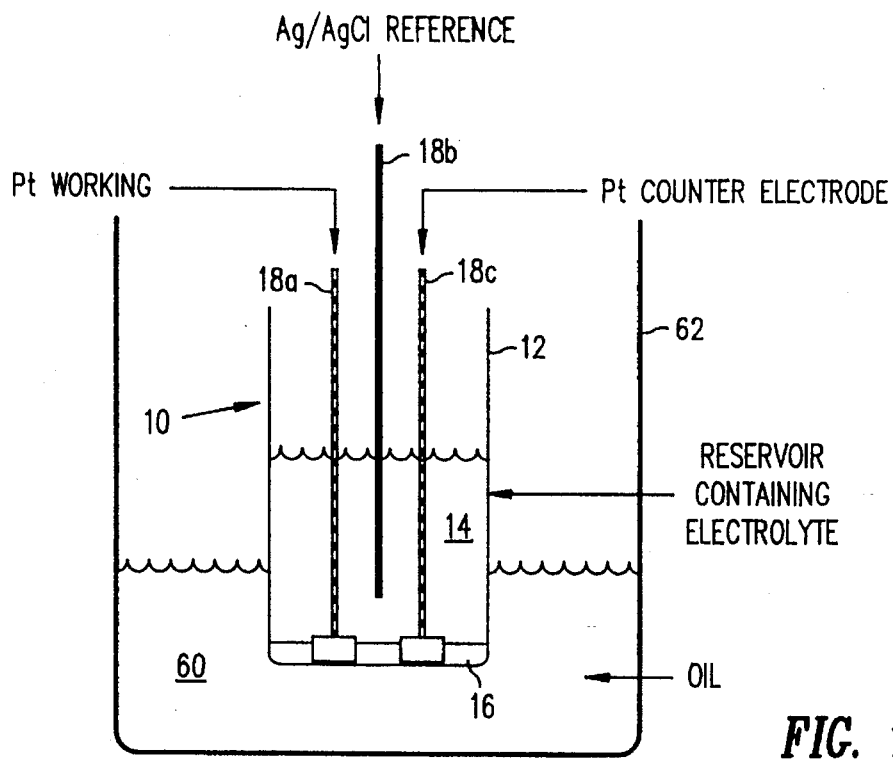
FIG. 1 is a side view of one embodiment of the sensor of the present invention used for direct measurement of a fluid having high resistivity, such as oil.

Referring to FIG. 1, there is shown one embodiment of the sensor 10 of the present invention immersed in a high resistivity liquid 60 to be tested. The liquid 60 can be oil or other organic fluids. The liquid 60 is contained in a vessel 62. The sensor 10 is placed in the liquid 60. By virtue of the sensor 10 being in the liquid 60, the sensor 10 is capable of detecting the presence of compounds in the liquid 60 directly and continuously. The resistivity of the liquid 60 is on the order of megaohms or higher. Although the sensor 10 is adapted to measure the presence of compounds in a high resistivity liquid 60, the sensor 10 can also be used with non-polar fluids 60 having low resistivity.

Figure 4:
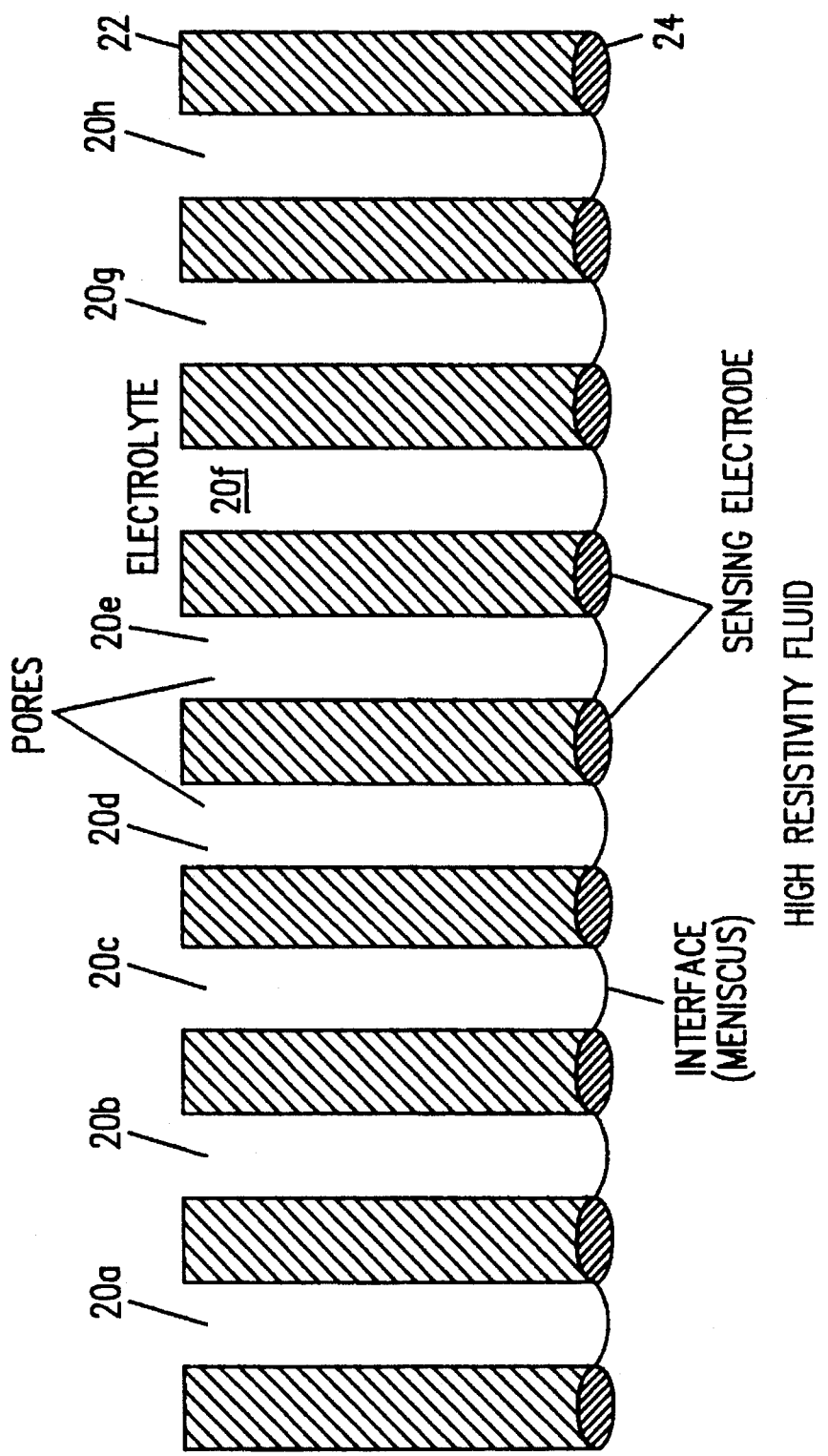
FIG. 4 is a detailed cross-sectional side view of the porous membrane of the sensor of FIG. 1.

The sensor 10 comprises a housing 12, such as glass cylinder or any other inert material, such as plastic, for containing an electrolytic solution 14. At one end of the housing 12 is a porous plate 16, such as porous ceramic. In the preferred embodiment, the porous plate 16 has a plurality of pores 20(a . . . h) which run through the porous plate 16 from the inner surface 22 to the outer surface 24. The pores 20(a–h) may be straight or tortuous paths. The plate 16 is made of a material with hydrophilic (polar) surfaces, that is, one that water and other polar electrolytes are capable of wetting. Examples of a material with hydrophilic surface includes porous alumina, porous (sintered) glass, porous hydrophilic plastic, or a silicon micromachined porous plate with a hydrophilic surface coating. The hydrophilic nature of the member 16 allows the electrolyte 14 to penetrate into the pores 20. However, the hydrophobic high resistivity liquid 60 does not "wet" the hydrophilic outer surface 24 of the plate 16 and therefore does not penetrate a great distance into the pores 20. The interface, as seen in FIG. 4, between the electrolyte 14 and the high resistivity liquid 60 is situated at or near the outer surface 24 of the plate 16 facing the high resistivity liquid 60 or slightly inside of the outer surface 24. The interface inside the pores 20 may be in the form of a curved surface called a meniscus. The exact shape of the meniscus is determined by the surface tension of the electrolyte 14 and the high resistivity liquid 60 and the plate material 16.

The porous plate 16 allows diffusions of compounds dissolved in the high resistivity liquid 60 into the electrolyte 14 across the interface between the electrolyte 14, and the high resistivity liquid 60. If there are compounds in the high resistivity liquid 60 which are soluble in the electrolyte 14, then those compounds would be extracted into the electrolyte 14 at the interface. Ideally, the porous plate 16 with its plurality of pores 20 allows a large area of contact between the two liquids in the pores 20 so that a high flux of material across the interface will be achieved.

A plurality of electrodes 18(a–c) are immersed in the electrolytic solution 14. In the embodiment shown in FIG. 1, three electrodes 18(a–c) are shown. The sensing electrode 18a can be made of a pH-sensitive material, such as iridium oxide. The change of the pH at electrodes 18 caused by the extraction of an acidic compound from the high resistivity liquid 60 into the electrolyte 14 can be sensed potentiometrically by monitoring the voltage between the sensing electrode 18a and the reference electrode 18b. Alternately, an electrical potential can be placed on the sensing electrode 18a by connecting the electrodes (the second electrode being an appropriate reference electrode 18b and the third optionally a counter electrode 18c) to a potentiostat or other potential-controlling device. The electrical potential must be sufficient to induce an electrochemical reaction to generate a current whose magnitude can be related to the concentration and/or the identity of the compound extracted from the high resistivity liquid 60. In addition, an alternating potential can be applied to the electrodes 18 and the resulting alternating current related to the concentration or identity of the compound extracted from the high resistivity liquid 60. The sensing electrode 18a is the only electrode that needs to be situated on the porous plate 16 so that the extracted compound can be detected as soon as it passes the high resistivity liquid 60/electrolyte 14 interface. The sensing electrode 18a can be situated either on the outer surface 24 of the porous plate 16 or the inner surface 22 of the plate 16. In the former case, the electrolytic contact between the sensing electrode and the other electrodes is made by the electrolyte 14 which is situated in the pores 20 of the plate 16. The other electrodes (reference and optional counter electrode) may be situated on the plate 16 or may be placed in contact with the electrolyte 14 anywhere inside the sensor housing 12. The reference electrode may be composed of silver/silver chloride (Ag/AgCl). The sensing electrode may be epoxied to the porous plate. Alternatively, it may be formed by sputtering onto the porous plate.

The electrolyte solution 14 consists of a polar solution into which is dissolved ionizable or dissociable species. The ions produced by the ionization or dissociation are capable of forming an electrolytic contact between the electrodes 18(a–c). The electrolytic solution may be composed of an aqueous solution, a sulfoxide based polar organic solvent, or carbonate based polar organic solvents. The sulfoxide based solvent may be dimethylsulfoxide and may contain lithium chloride. Alternately, the electrolyte 14 can be a polar polymer electrolyte.

Figure 2:
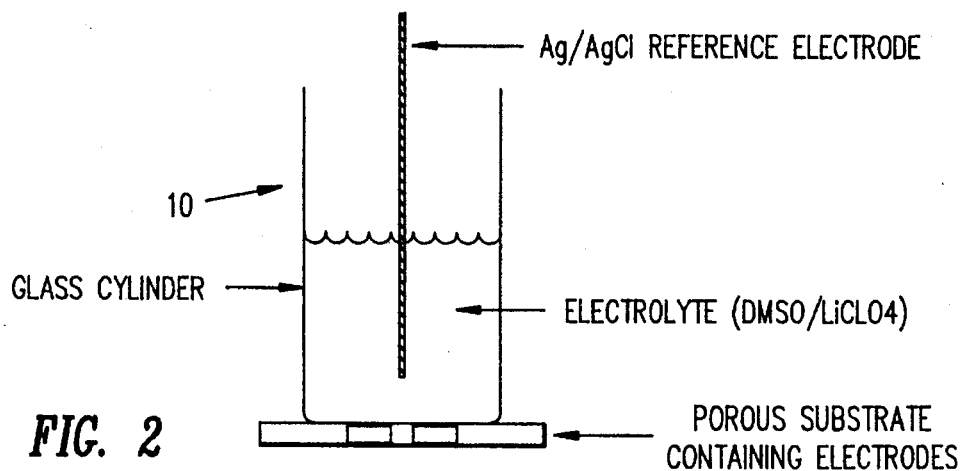
FIG. 2 is a side view of the sensor of FIG. 1.
Figure 3:
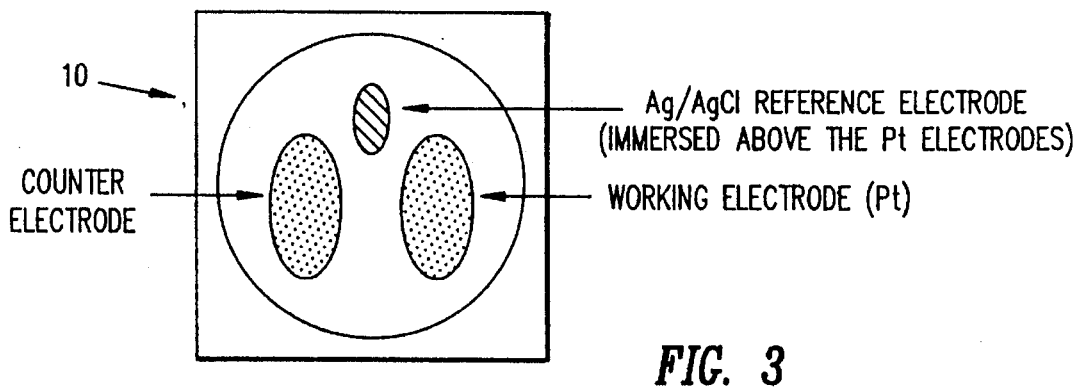
FIG. 3 is an end view of the sensor of FIG. 1.

Referring to FIGS. 2 and 3, there is shown respectively a side and an end view of the embodiment of the sensor 10 shown in FIG. 1. The electrodes 18a and 18c are deposited on one side of the membrane 16 and form an interface with the liquid 60. At the location of the electrode 18a and 18c, triple points are formed, i.e. the position of the location of electrodes 18a and 18c is the interface of the electrodes 18(a and c), electrolytic solution 14, and the liquid 60.

In the operation of the sensor 10 of the present invention, at the triple point location, the liquid 60 is in contact with the electrolytic solution 14. This contact enables polar compounds dissolved in the liquid 60 which are also soluble in the electrolytic solution 14 to be extracted into the electrolytic solution 14. At the same time, and being proximate to the electrodes 18(a and c), the detection of these compounds extracted into the electrolytic solution 14 by the electrodes 18(a–c) can be accomplished.

In addition, since the electrolytic solution 14 is not miscible with the liquid 60, the liquid 60 itself will not be dissolved into the electrolytic solution 14.

Figure 5:
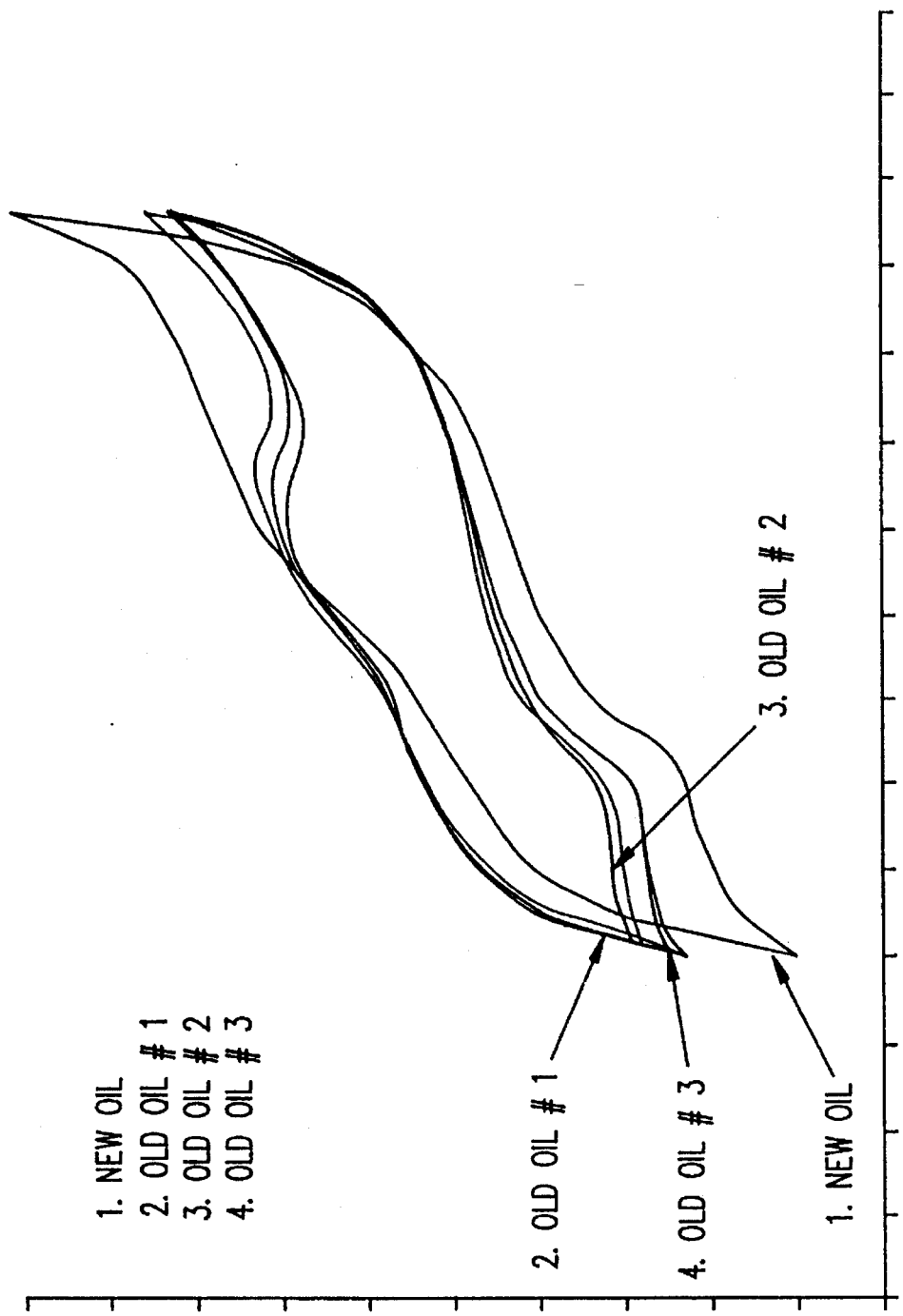
FIG. 5 is a cyclic voltammogram of four different types of oil showing changes in the concentration of substances in the oil as its ages.

Referring to FIG. 5, there is shown cyclic voltammograms of four different types of oils that have been analyzed using the sensor 10 of the present invention. The X axis represents applied potential (V) with the Y axis representing current in micro amps. As can be seen from the graph shown in FIG. 5, changes in the composition of the liquid 60, such as oil, can be detected by in situ extraction and electrochemical measurement using the sensor 10. Thus, an on-line sensor 10, placed in a vessel 62, containing oil 60 can detect changes in the properties of oil, such that maintenance or other actions can be initiated.

The sensor 10 shown in FIGS. 1–4 represent an amperometric type sensor. The working electrode 18a can be replaced by an indicator electrode, made for example from a pH sensitive material such as iridium oxide to make a pH sensor. A voltage is then measured between the indicator electrode and the reference electrode 18b to accomplish potentiometric or pH measurement.

The sensor design of the present invention does away with the use of tedious pre-extraction of the electroactive species. It is therefore highly suited for direct in situ monitoring of oil quality.

What is claimed is:

1. An apparatus for directly measuring electrochemical properties of compounds in a high resistivity liquid comprising:

(a) an electrolytic solution;

(b) a housing including a hydrophilic membrane having a plurality of pores for containment of said electrolytic solution and for immersion in said high resistivity liquid;

(c) said hydrophilic membrane for permitting passage of a portion of said electrolytic solution into said plurality of pores and for preventing substantial passage of said high resistivity liquid into said pores thereby facilitating the formation of an interface between said electrolytic solution and said high resistivity liquid in each of said plurality of pores and allowing extraction of said compounds in said high resistivity liquid into said electrolytic solution; and (d) a plurality of electrodes, including a porous sensing electrode, immersed in said electrolytic solution with at least the sensing electrode positioned directly on said membrane in proximate relationship to said interface between said electrolytic solution and said high resistivity liquid for detecting and measuring the concentration of said compounds extracted from the high resistivity fluid into the electrolytic solution.

2. The apparatus of claim 1 wherein said electrolytic solution is composed of a polar solvent.

3. The apparatus of claim 2 wherein said electrolytic solution is composed of an aqueous solution.

4. The apparatus of claim 3 wherein said electrolytic solution is composed of a sulfoxide based polar organic solvent.

5. The apparatus of claim 4 further having lithium chlorate added to the sulfoxide based polar organic solvent.

6. The apparatus as recited in claim 5 wherein said sulfoxide based polar organic solvent is dimethylsulfoxide.

7. The apparatus of claim 1 wherein said electrolytic solution is composed of carbonate based polar organic solvents.

8. The apparatus of claim 1 wherein said housing is a glass cylinder.

9. The apparatus of claim 1 wherein said plurality of electrodes comprises a reference electrode and a sensing electrode.

10. The apparatus of claim 9 wherein said reference electrode is composed of silver/silver chloride (Ag/AgCl).

11. The apparatus of claim 1 wherein said electrodes are sputtered onto the porous membrane.

12. The apparatus of claim 1 wherein said sensing electrode is epoxied to said permeable membrane.

* * * * *